United States Patent
Katz et al.

(10) Patent No.: US 11,112,394 B2
(45) Date of Patent: Sep. 7, 2021

(54) ETHYLENIC COMPOUND SENSOR INCLUDING AN ORGANIC SEMICONDUCTOR

(71) Applicant: JOHNS HOPKINS TECHNOLOGY VENTURES, Baltimore, MD (US)

(72) Inventors: Howard E. Katz, Baltimore, MD (US); Kalpana Besar, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 502 days.

(21) Appl. No.: 15/852,063

(22) Filed: Dec. 22, 2017

(65) Prior Publication Data

US 2018/0180584 A1   Jun. 28, 2018

Related U.S. Application Data

(60) Provisional application No. 62/438,576, filed on Dec. 23, 2016.

(51) Int. Cl.
| | |
|---|---|
| *G01N 33/00* | (2006.01) |
| *H01L 51/00* | (2006.01) |
| *H01L 29/423* | (2006.01) |
| *H01L 27/28* | (2006.01) |
| *H01L 51/05* | (2006.01) |
| *H01L 21/02* | (2006.01) |

(52) U.S. Cl.
CPC ....... *G01N 33/0047* (2013.01); *H01L 27/283* (2013.01); *H01L 29/42316* (2013.01); *H01L 51/0034* (2013.01); *H01L 51/0566* (2013.01); *H01L 21/02164* (2013.01); *H01L 51/0036* (2013.01); *H01L 51/0545* (2013.01)

(58) Field of Classification Search
CPC ...... G01N 33/0047; G01N 27/414–417; H01L 27/283; H01L 29/42316; H01L 29/2924; H01L 29/13073; H01L 51/0036; H01L 51/0545

See application file for complete search history.

(56) References Cited

U.S. PATENT DOCUMENTS

| | | | |
|---|---|---|---|
| 2002/0105080 A1* | 8/2002 | Speakman | B41J 2/01 257/749 |
| 2005/0129573 A1* | 6/2005 | Gabriel | B82Y 10/00 422/400 |

(Continued)

OTHER PUBLICATIONS

Eyal et al., Journal of Applied Polymer Science, 1992, 1065-1074 (Year: 1992).*

(Continued)

*Primary Examiner* — Gurpreet Kaur
(74) *Attorney, Agent, or Firm* — Tarolli, Sundheim, Covell & Tummino LLP

(57) ABSTRACT

An ethylene-sensitive sensor is described that includes a power source; an ethylene-sensitive semiconductor component electrically connected to the power source, the semiconducting component comprising a semiconducting organic compound; an input electrode electrically connected to the semiconductor component; and an output electrode electrically connected to the semiconductor component. The semiconductor material is at least partially exposed such that it can be contacted by a vapor. Methods of using the ethylene-sensitive sensor to detect ethylenic compounds are also described.

16 Claims, 8 Drawing Sheets

(56) References Cited

U.S. PATENT DOCUMENTS

| | | | | |
|---|---|---|---|---|
| 2007/0114138 A1* | 5/2007 | Krasteva | ............ | G01N 27/127 205/787 |
| 2008/0017507 A1* | 1/2008 | Ramamurthy | ....... | G01N 27/126 204/400 |
| 2009/0068758 A1* | 3/2009 | Karim | ...................... | B01J 20/26 436/501 |
| 2013/0161599 A1* | 6/2013 | Katz | .................. | H01L 51/0558 257/40 |
| 2013/0273665 A1* | 10/2013 | Swager | ................ | G01N 27/125 436/142 |

OTHER PUBLICATIONS

Besar, Kalpana, et al. "Printable ammonia sensor based on organic field effect transistor." Organic Electronics 15.11 (2014): 3221-3230.

Durgun, Engin, et al. "Transition-metal-ethylene complexes as high-capacity hydrogen-storage media." Physical review letters 97.22 (2006): 226102.

Esser, Birgit, Jan M. Schnorr, and Timothy M. Swager. "Selective Detection of Ethylene Gas Using Carbon Nanotube-based Devices: Utility in Determination of Fruit Ripeness." Angewandte Chemie International Edition 51.23 (2012): 5752-5756.

Huang, Weiguo, et al. "Highly sensitive NH3 detection based on organic field-effect transistors with tris(pentafluorophenyl) borane as receptor." Journal of the American Chemical Society 134.36 (2012): 14650-14653.

Kathirvelan, Jayaraman, and Rajagopalan Vijayaraghavan. "Development of prototype laboratory setup for selective detection of ethylene based on multiwalled carbon nanotubes." Journal of Sensors 2014 (2014).

Khim, Dongyoon, et al. "Precisely controlled ultrathin conjugated polymer films for large area transparent transistors and highly sensitive chemical sensors." Advanced Materials 28.14 (2016): 2752-2759.

Ma, Li-Juan, et al. "Ti-?2-(C2H2) and HCC—TiH as high capacity hydrogen storage media." International Journal of Hydrogen Energy 38.36 (2013): 16185-16192.

Valencia, Hubert, Adrià Gil, and Gilles Frapper. "Trends in the hydrogen activation and storage by adsorbed 3d transition metal atoms onto graphene and nanotube surfaces: A DFT study and molecular orbital analysis." The Journal of Physical Chemistry C 119.10 (2015): 5506-5522.

* cited by examiner

ETHYLENIC COMPOUND SENSOR INCLUDING AN ORGANIC SEMICONDUCTOR

CONTINUING APPLICATION DATA

This application claims the benefit of U.S. Provisional Application Ser. No. 62/438,576, filed Dec. 23, 2016, the disclosure of which is incorporated by reference herein.

BACKGROUND

Ethylene is a small hydrocarbon with no odor or color. It occurs naturally as a plant hormone, it regulates various physiologically important events like germination, development or growth of the plant flowering and most importantly the ripening and subsequently senescence of the fruits post harvesting, especially climacteric fruits. Abeles, F B, Morgan, P W, Saltveit, M E, "Ethylene in Plant Biology"; Academic Press, San Diego, 1973.

Specific pathways and the role of ethylene in a plant's life cycle have been thoroughly investigated considering the multimillion dollar losses to the horticulture industry due to premature deterioration or overripening of fruits and flowers during transportation and storage. Ethylene is produced as a product of biosynthesis in plants; it permeates cells and triggers the fruit-ripening gene resulting in change in texture, color and taste of the fruits. Ripened fruit produces more ethylene which in turn induces more ripening and ultimately rotting of the fruits. By measuring the concentration of ethylene in the vicinity of the fruits at a particular time, one can figure the approximate stage of ripeness of the fruit. The whole process can theoretically be controlled by monitoring the ambient condition maintained in the storage units and thus increase the shelf life of the fruits. By maintaining the storage unit temperature close to 0° C., oxygen levels to 1 to 2%, high humidity nearing 92% and carbon dioxide levels to 200 ppm, fruits and vegetables can be successfully stored for weeks or potentially months. While monitoring these conditions is relatively straightforward, developing a suitable sensing platform for ethylene is still a challenge owing to the small molecular size and very limited physiochemical reactivity.

Existing ethylene sensing technologies include photoacoustic spectroscopy, gas chromatography, metal-oxide semiconductor-based sensors, electrochemical sensors, electro-catalytic sensors, and non-dispersive spectroscopy. Present techniques are either too expensive, too bulky, require high temperature or do not have high sensitivity. Very recently, Esser et al. developed a reversible chemiresistive sensor based on single walled carbon nanotubes modified by a copper(I) complex to enhance selectivity. The sensor could detect ethylene concentrations ranging from 0.5 to 50 ppm. Esser et al., Angew. Chemie-Int. Ed., 51, 5752-5756 (2012). Following this work Kathirvelam et al. published a multi-walled carbon nanotube sensor for ethylene on a flexible substrate. They report a sensitivity of 20 ppm and the response to be 10 times higher than the earlier single wall carbon nanotube sensor report, however no selectivity studies were reported. Kathirvelan, J., Vijayaraghavan, R., J. Sensors 2014, 1-6 (2014). Selectivity is a major concern for the carbon nanotube based sensor devices due to various Van der-Waals interactions on carbon nanotube surface. Although Esser et al. included a selectivity study, several gases like acetonitrile (100 ppm), tetrahydrofuran (200 ppm) and acetaldehyde (75 ppm) had much higher response than the reported lower limit of 1 ppm for ethylene and almost equal response to 20 ppm ethylene, which can be a major problem for practical application of these devices where a high selectivity is of utmost importance. Another major hindrance for the commercialization of the carbon nanotube based sensor is the cost of production and separation of semiconducting and conductive nanotubes, which continues to be a challenge to the research community despite extensive investigation.

Over the past few years, organic field effect transistors have received much attention for their potential in sensing applications due to their easy processibility, which makes them both time and cost efficient. Developing a suitable sensing platform for ethylene is still a challenge owing to its small size and very limited physiochemical reactivity. Dongyoon Khim et al. recently reported the very first organic field effect ethylene sensor. Khim et al., Adv Mater., 28(14), 2752-9 (2016). Using a precise bar-coating method, they were able to detect 1000 ppm of ethylene. However, there remains a need for sensors for ethylenic compounds, particularly sensors having higher sensitivity.

SUMMARY OF THE INVENTION

In one aspect, the present invention provides an ethylene-sensitive sensor, comprising: a power source; an ethylene-sensitive semiconductor component electrically connected to the power source, the semiconducting component comprising a semiconducting organic compound; an input electrode electrically connected to the semiconductor component; and an output electrode electrically connected to the semiconductor component; wherein the semiconductor material is at least partially exposed such that it can be contacted by a vapor.

In some embodiments, the ethylene-sensitive semiconductor component is part of a field effect transistor. In further embodiments, the ethylene-sensitive sensor comprises a gate electrode. In other embodiments, the semiconducting polymer, the input electrode, and the output electrode, are in contact with a silicon dioxide layer positioned over a silicon layer. In further embodiments, the ethylene-sensitive sensor is flexible.

The ethylene-sensitive sensor can include a variety of different semiconducting organic compounds. In some embodiments, the semiconducting organic compound is a p-type organic semiconductor. In further embodiments, the semiconducting organic compound includes an organic group selected from group consisting of thiophene, phenylene, selenophene, fluorene, naphthalene, ethylene, ethynylene, cyclopentadiene, silacyclopentadiene, benzothiadiazole, benzoxadiazole, diketopyrroleopyrrole, and isoindigo. In additional embodiments, the semiconducting organic compound is a semiconducting polymer. For example, the semiconducting polymer can be a thiophene polymer, such as poly(3-hexylthiophene-2,5-diyl) (P3HT) or poly(3,3'''-didodecylquarterthiophene) (PQT12).

In some embodiments, the ethylene-sensitive semiconductor component includes a porogen. For example, the porogen can be N-(tert-butoxy-carbonyloxy)-phthalimide. In additional embodiments, the ethylene-sensitive semiconductor component includes transition metal particles. For example, the transition metal particles can be palladium particles.

In another aspect, the invention provides a method of detecting an ethylenic compound using the ethylene-sensitive sensor as described herein, comprising contacting a vapor of interest with the ethylene-sensitive sensor having an output voltage or current, and determining that an ethylenic compound is present in the vapor of interest if this contact causes a change in the output voltage or current of the ethylene-sensitive sensor.

In some embodiments, the semiconductor component of the ethylene-sensitive sensor is part of a field effect transistor. In further embodiments, the semiconductor component of the ethylene-sensitive sensor is a semiconducting polymer including a porogen and transition metal particles. In some embodiments, the ethylenic compound is ethylene. In further embodiments, the vapor of interest is produced by fruit. In some embodiments, the method of detecting the ethylenic compound includes the step of determining the amount of ethylenic compound present in the vapor. In further embodiments, a concentration of 50 ppm or more of the ethylenic compound is sufficient to cause a detectable change in the output voltage or current of the ethylene-sensitive sensor.

BRIEF DESCRIPTION OF THE FIGURES

The present invention may be more readily understood by reference to the following drawings wherein.

Figure 1:
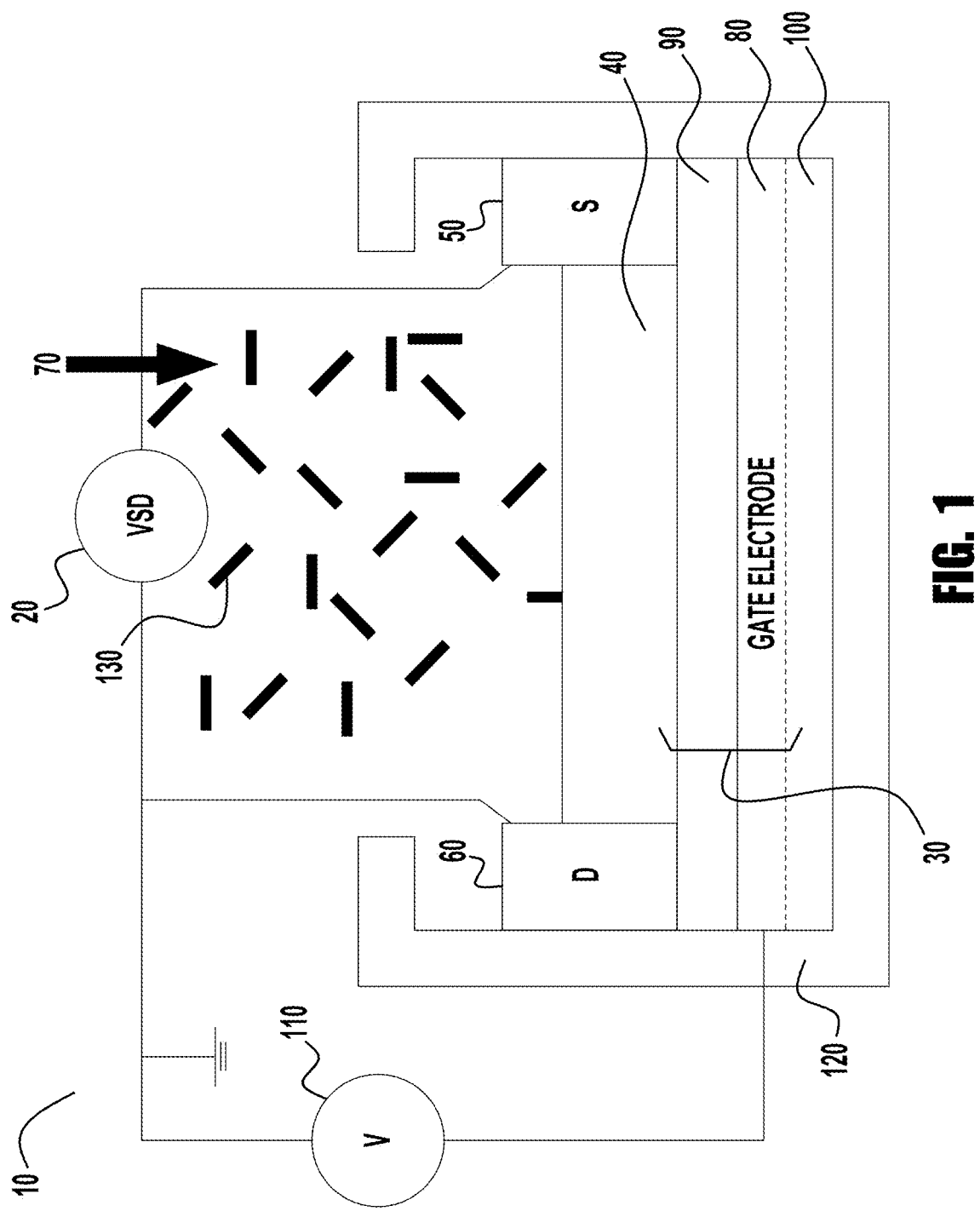
FIG. 1 provides a schematic diagram of an ethylene-sensitive sensor in contact with a vapor including an ethylenic compound.

To illustrate the invention, several embodiments of the invention will now be described in more detail. Reference will be made to the drawings, which are summarized above. Skilled artisans will recognize the embodiments provided herein have many useful alternatives that fall within the scope of the invention.

DETAILED DESCRIPTION OF THE INVENTION

An ethylene-sensitive sensor is described that includes a power source; an ethylene-sensitive semiconductor component electrically connected to the power source, the semiconducting component comprising a semiconducting organic compound; an input electrode electrically connected to the semiconductor component; and an output electrode electrically connected to the semiconductor component. The semiconductor material is at least partially exposed such that it can be contacted by a vapor. Methods of using the ethylene-sensitive sensor to detect ethylenic compounds are also described.

Definitions

Unless otherwise defined, all technical and scientific terms used herein have the same meaning as commonly understood by one of ordinary skill in the art to which this invention pertains. In case of conflict, the present specification, including definitions, will control.

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

The terms "comprising" and variations thereof do not have a limiting meaning where these terms appear in the description and claims.

Also herein, the recitations of numerical ranges by endpoints include all numbers subsumed within that range (e.g., 1 to 5 includes 1, 1.5, 2, 2.75, 3, 3.80, 4, 5, etc.).

Electronic sensors have the advantage that they can be monitored using inexpensive equipment and produce outputs that are easily analyzed and archived by computers. In order to achieve electronic sensing of ethylenic vapors, it is necessary that the ethylenic compound interact with a circuit element so that the impedance of the element changes. One means of doing this is to have the ethylenic compound interact with a material in the circuit element so that the electronic structure of the material changes. This can occur when the ethylenic double bond interacts with a component of the circuit element material. One example of such an interaction is a pi-pi interaction between the ethylenic compound and a pi system in the material. Another example is a ligand-metal interaction between the ethylenic double bond acting as a ligand and a metal atom in the material. In one embodiment, this invention demonstrates that a combination of these two interactions can enhance the electronic response of a semiconducting organic compound to ethylene vapor present at a concentration of at least as little as 50 ppm.

In various embodiments, the semiconducting organic compound can function as a conductor or semiconductor as part of a simple resistor or a field-effect transistor. The semiconducting organic compound is a conjugated organic or polymer semiconductor, and particularly the organic compounds known as metal phthalocyanines that have metal atoms as possible coordination sites, or a polymer such as P3HT. The polymer semiconductor may be combined with metal particles, in particular, palladium particles, to form a semiconducting composite.

Ethylene-Sensitive Sensor

In one aspect, the present invention provides an ethylene-sensitive sensor 10. An embodiment of the ethylene-sensitive sensor is shown in FIG. 1. The ethylene-sensitive sensor 10 includes a power source 20; an ethylene-sensitive semiconductor component 30 electrically connected to the power source 20, the semiconducting component 30 comprising a semiconducting organic compound 40; an input (i.e., source) electrode 50 electrically connected to the semiconductor component 30; and an output (i.e., drain) electrode 60 electrically connected to the semiconductor component 30; wherein the semiconductor material is at least partially exposed such that it can be contacted by a vapor 70.

In some embodiments, the ethylene-sensitive semiconductor component is part of a field effect transistor. In a field effect transistor, a gate electrode 80 is included, with an associated gate voltage source 110. In other embodiments, the semiconducting polymer 40, the input electrode 50, and the output electrode 60, are in contact with a silicon dioxide layer 90 positioned over a silicon layer 100. A separate gate electrode 80 can be included in some embodiments, or the silicon layer 100 can be doped so that it can function as a gate electrode. In further embodiments, the ethylene-sensitive sensor 10 is flexible. The ethylene-sensitive sensor 10 can also include an enclosure 120 that provides protection for the sensor while allowing contact with the outside environment.

The ethylene-sensitive sensor detects the presence of one or more ethylenic compounds 130. Preferably the ethylenic compounds exist in a vapor 70 that can readily contact the surface of the semiconductor component 30 of the sensor, and in particular the semiconducting polymer 40. Ethylenic compounds are compounds including the ethylene functional group. Ethylene (IUPAC name: ethene) is a hydrocarbon including a double bond which has the formula $C_2H_4$. Preferably the ethylenic compound is a small molecule having a mass of 500 daltons or less.

The Semiconductor Component

The ethylene-sensitive sensor includes a semiconductor component, which electrically responds to the presence of an ethylenic compound (e.g., ethylene vapor). The semiconductor component is typically a thin layer of semiconducting organic material that can include other features such as pores or transition metal particles to increase the effectiveness of the semiconducting organic material. The semiconducting organic material can be deposited in a thin layer using methods such as spincoating and printing. In some embodiments, the layer of material is from 20 to 200 nm thick, while in other embodiments the layer of material is from 50 to 200 nm thick, or 20 to 100 nm thick.

The ethylene-sensitive sensor can include a variety of different semiconducting organic compounds. In some embodiments, the semiconducting organic compound is a p-type organic semiconductor. In further embodiments, the semiconducting organic compound includes an organic group selected from the group consisting of thiophene, phenylene, selenophene, fluorene, naphthalene, ethylene, ethynylene, cyclopentadiene, silacyclopentadiene, benzothiadiazole, benzoxadiazole, diketopyrroleopyrrole, and isoindigo. These organic groups can form part of an organic small molecule, or part of a polymer. In additional embodiments, the semiconducting organic compound is a semiconducting polymer. For example, the semiconducting polymer can be a thiophene polymer, such as poly(3-hexylthiophene-2,5-diyl) (P3HT) or poly(3,3'''-didodecylquarterthiophene) (PQT12).

In some embodiments, the ethylene-sensitive semiconductor component includes a porogen. Porogens are compounds that can be added to the semiconducting organic compound to introduce pores into the material, thereby increasing its surface area and the interaction area of the compound layer. For example, the porogen can be N-(tert-butoxy-carbonyloxy)-phthalimide or tert-butyl phenyl carbonate.

In additional embodiments, the ethylene-sensitive semiconductor component includes transition metal particles. In some embodiments, the metal particles have an average diameter of less than 1 micron. For example, the transition metal particles can be palladium particles. The amount of metal particles can be up to 10%, up to 25%, up to 50%, or up to 100% of the weight of the semiconducting organic compound that is also included in the semiconductor component.

Electrodes

The ethylene sensor includes an input electrode and an output electrode, which are electrically connected to the semiconductor component and typically are placed on opposite sides of the semiconductor component. The input electrode is electrically connected to the power source (e.g., a potentiostat). The output electrode is connected to a display, alarm, and/or processing module that evaluates or responds to the output signal from the ethyelene-sensor. In further embodiments, the ethylene sensor includes a gate electrode, positioned under the silicon dioxide layer and electrically connected to a gate voltage source.

Electrode(s) are fabricated using the methods and materials known in the art. Non-limiting examples of electroconductive material suitable for electrode construction on the substrate layer include Copper, Nickel, Tin, Gold, Platinum, Stainless Steel, and conductive inks such as carbon ink or Ag ink. In some embodiments, the electrode(s) are thin sheets of metal that are placed in contact with the semiconducting organic compound. In other embodiments, other methods of constructing the electrodes on the macroporous layer can be used. Non-limiting examples of constructing the electrodes on the substrate layer include ion beam techniques, etching, and self-assembly.

Enclosure for the Ethylene-Sensitive Sensor

In some embodiments, the ethylene-sensitive sensor is held within an enclosure. The enclosure provides support and protection for the invention, while including an opening to assure that the semiconductor material is at least partially exposed such that it can be contacted by a vapor. The enclosure should also provide access to the circuitry contacting the input and output electrodes, and possible circuitry to connect the sensor with a processing module.

The enclosure may be formed of any suitable material or combination of suitable materials. Suitable materials may include elastomers, such as polydimethylsiloxane (PDMS); plastics, such as acrylic, polystyrene, polypropylene, polycarbonate, polymethyl methacrylate, etc.; glass; ceramics; sol-gels; silicon and/or other metalloids; metals or metal oxides; etc.

The enclosure for the ethylene sensor may be fabricated by any suitable mechanism, based on the desired application for the system and on materials used in fabrication. In some embodiments, the enclosure and its features can be fabricated using a water jet cutter. In other embodiments, one or more components may be molded, stamped, and/or embossed using a suitable mold. Such a mold may be formed of any suitable material by micromachining, etching, soft lithography, material deposition, cutting, and/or punching, among others. Alternatively, or in addition, components of the enclosure may be fabricated without a mold by etching, micromachining, cutting, punching, and/or material deposition.

In various embodiments, a processing module is included with the ethylene-sensitive sensor. The processing module receives data from the sensor via conventional circuitry. In one embodiment, the processing module compares the detection data against expected characteristic transistor responses and indicates when they do not match. The processing module may be embodied as a central processing unit (CPU), a microcontroller, a microprocessor, a digital signal processor (DSP), a state machine, a programmable logic device, an application specific integrated circuit (ASIC), a general-purpose computing device, or other device known in the art.

Methods of Detecting Ethylenic Compounds

In another aspect, the invention provides a method of detecting an ethylenic compound using the ethylene-sensitive sensor as described herein, comprising contacting a vapor of interest with the ethylene-sensitive sensor having an output voltage or current, and determining that an ethylenic compound is present in the vapor of interest if this contact causes a change in the output voltage or current of the ethylene-sensitive sensor. In some embodiments, the voltage or current increases in response to the presence of an ethylenic compound, while in other embodiments the voltage or current decreases in response to the presence of the ethylenic compound.

In some embodiments, the semiconductor component of the ethylene-sensitive sensor is part of a field effect transistor. In further embodiments, the semiconductor component of the ethylene-sensitive sensor is a semiconducting polymer including a porogen and transition metal particles. In some embodiments, the ethylenic compound is ethylene. In further embodiments, the vapor of interest is produced by fruit. In some embodiments, the method of detecting the ethylenic compound includes the step of determining the amount of ethylenic compound present in the vapor. In further embodiments, a concentration of 25 ppm or more, 50 ppm or more, or 100 ppm or more of the ethylenic compound is sufficient to cause a detectable change in the output voltage or current of the ethylene-sensitive sensor. In additional embodiments, the ethylene-sensitive sensor is re-usable, so that it can be restored to a sensitive state after initial exposure to an ethylenic compound.

Examples have been included to more clearly describe particular embodiments of the invention. However, there are a wide variety of other embodiments within the scope of the present invention, which should not be limited to the particular example provided herein.

EXAMPLES

Example 1—Ethylene Detection Based on Organic Field Effect Transistors with Porogen and Palladium Particle Receptor Enhancements Ethylene sensing is a highly challenging problem for the horticulture industry owing to the limited physiochemical reactivity of ethylene. In one embodiment, the inventors have provided a poly(3-hexylthiophene-2,5-diyl) (P3HT) based organic field effect transistor as a sensing platform for ethylene with sensitivity of 25 ppm V/V. N-(tert-Butoxycarbonyloxy)-phthalimide porogen to increase surface area and palladium particle receptors to increase ethylene binding were used as additives to the P3HT film. Both modifications give statistically significant sensitivity increases over pure P3HT. The sensor response is reversible and is also highly selective for ethylene compared to common solvent vapors.

A sensitive organic field effect transistor (OFET) based sensing platform (FIG. 1) for ethylene using a semiconducting organic compound such as poly(3-hexylthiophene-2,5-diyl) (P3HT) as an ethylene receptor is described herein. The semiconducting organic compound can include transition metals to increase sensitivity to ethylene. P3HT alone is not specifically designed to sense ethylene; rather our main goal herein is the introduction of both pores and specific metal particles to markedly increase the detection abilities of this prototypical material. A related interaction between transition metals and the hydrogen atom has been studied extensively in the context of hydrogen storage, to be used as an alternative and renewable fuel. Valencia et al., J. Phys. Chem. C, 119, 5506-5522 (2015). There are reports indicating that hydrocarbons like ethylene have an affinity to bind with transition metals and form complexes, which then can be used to successfully store hydrogen. Ma et al., Int. J. Hydrogen Energy, 38, 16185-16192 (2013). Palladium, platinum, zirconium and titanium have been proposed for this application. In a report by Durgun et al binding between titanium and ethylene had been studied thoroughly. Durgun et al., Phys. Rev. Lett., 97, 1-4 (2006). The paper stated that a single Ti-atom could bond to an ethylene molecule to form a $C_2H_4Ti$ complex without any input energy. However, considering the practical limitations like stability under ambient condition and handling, palladium was chosen as the potential receptor metal for ethylene.

Ethylene is not a very strongly interactive analyte and can only affect the sensing membrane via weak interactions with delocalized double bond electrons in the semiconductor. P3HT was chosen as the primary organic semiconductor layer for this study as it has been well established for sensing ammonia. Besar et al., Org. Electron., 15, 3221-3230 (2014). The lone pairs on ammonia molecules trap the hole carriers in the p-type semiconductor, effectively decreasing the mobility and/or mobile charge density. Ethylene should have similar interaction (electron donating tendency, although less strong) with the semiconductor layer because of its slightly nucleophilic double bond.

Ethylene response was monitored by investigating the percentage change in drain current of the P3HT based transistors (with and without palladium particles) upon exposure to 25-ppm ethylene. An average decrease of 14.6% in drain current was observed on exposure to 25-ppm ethylene gas for 5 minutes (FIGS. 2b and 2c), consistent with the expected mechanism. The response was reversible under ambient conditions, also expected because of the weak ethylene-P3HT interactions.

Devices were also exposed to nitrogen (used as the balance gas for the ethylene mixture) as a control; only a 4% drain current decrease was observed. The current decrease on exposure to nitrogen is considerably smaller than ethylene exposure and it can be attributed to the displacement of oxygen molecules from the P3HT film due to nitrogen flow.

Figure 2A:
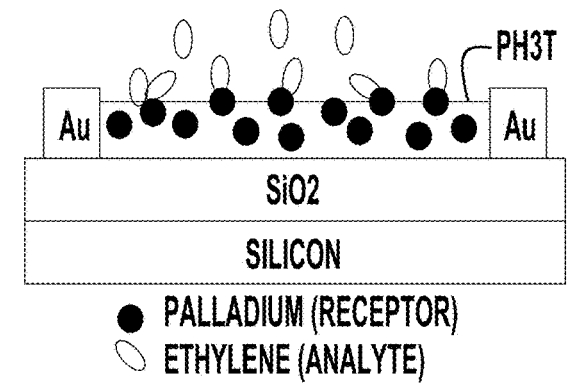
FIGS. 2A-2C provide (a) Schematic of OFET device sensing ethylene gas. (b) Typical transfer curve and analysis of standard P3HT device be-fore and after exposure to ethylene. "Normalized" means corrected for projected drift (c) Average percent decreases in current for each type of sensor (P3HT, with addition of porogen, and with addition of both porogen and palladium particles) when exposed to 25 ppm ethylene for five minutes.
Figure 2B:
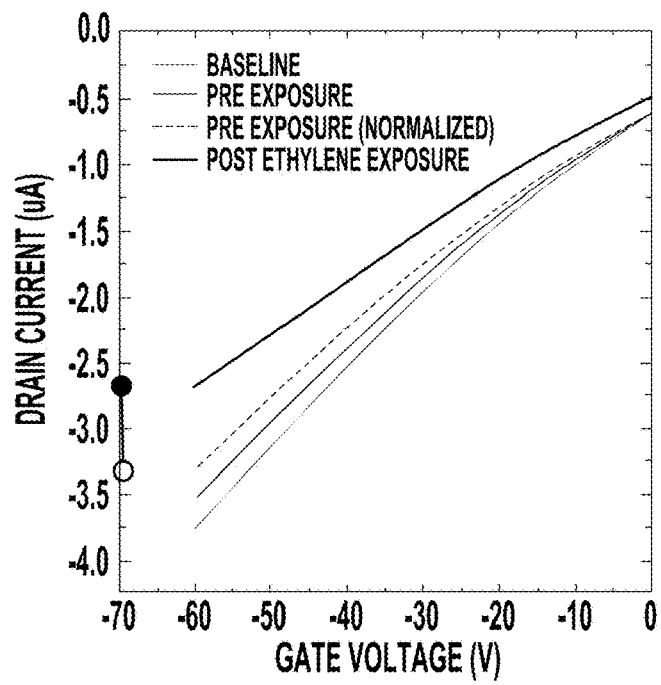

FIG. 2b shows a typical example of sensing data based on a simple P3HT sensor without added porogen or palladium particles. The difference between the baseline and pre-exposure curves allow us to normalize the data based on the reproducible slight changes of this type of OFET in air. The final curve is taken immediately following exposure to ethylene. The percentage decrease in current is calculated based on the drain current measured when the gate voltage is at −60V.

Figure 2C:
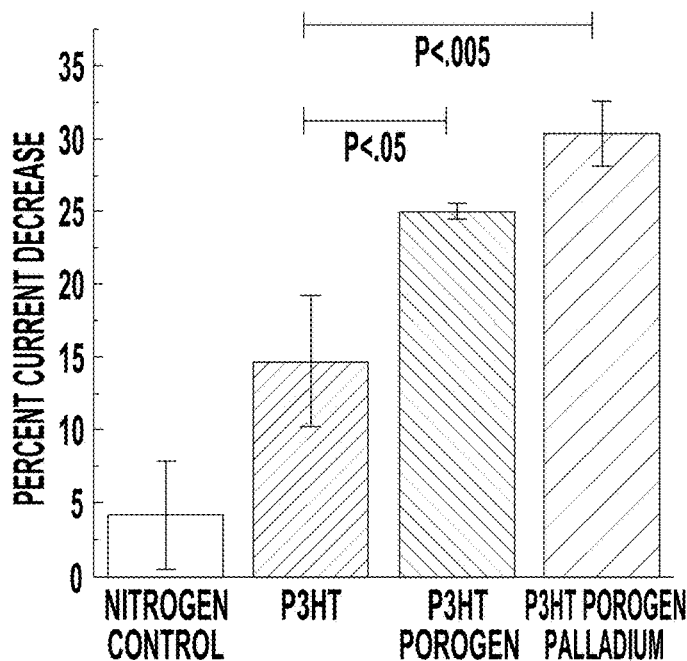
Figure 3A:
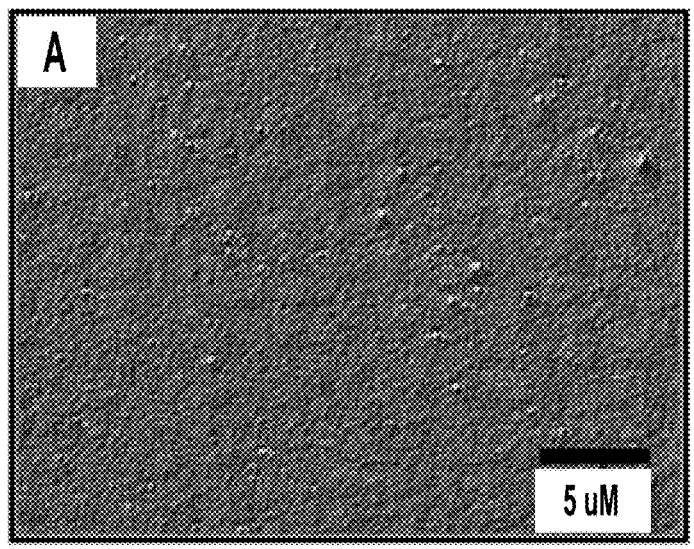
FIGS. 3A-3C provide differential interference contrast (DIC) images taken on laser optical microscope at 100× magnification of (a) plain P3HT surface, (b) P3HT surface with N-(tert-butoxy-carbonyloxy)-phthalimide porogen, and (c) P3HT surface with porogen and palladium particles.
Figure 3B:
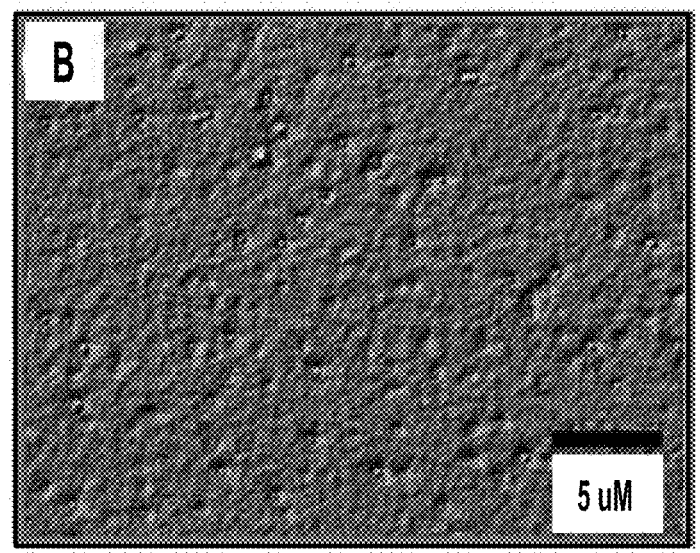
Figure 3C:
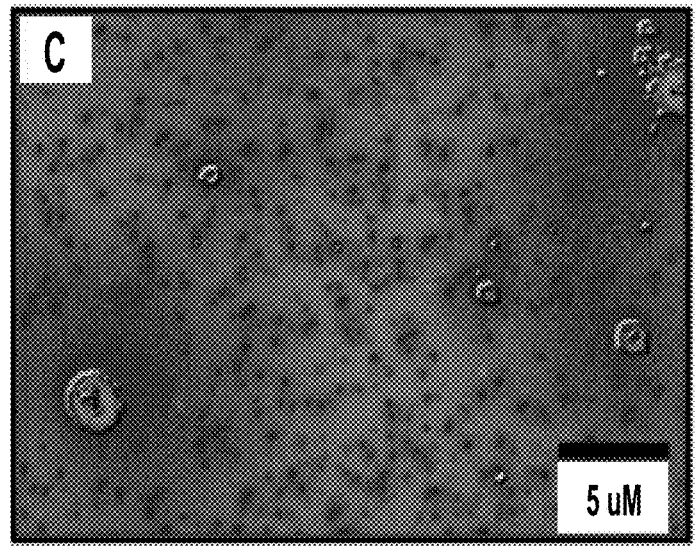

A simple approach to increase the response of any gas sensor is to increase the interaction area of the sensitive film, which would increase the permeation of the gas molecules into the films and add sites for chemical interaction. There are reports stating that adding polystyrene beads increases the surface area and the adsorption of ethylene molecules in a carbon nanotube-based sensor and thus results in an overall increase in the response to ethylene. In order to investigate the influence of the film porosity for P3HT film, tert-butyl phenyl carbonate (25 V/V %) and N-(tert-butoxy-carbonyloxy)-phthalimide (25 wt %) were added to the P3HT coating solution. Both tert-butyl phenyl carbonate and N-(tert-butoxy-carbonyloxy)-phthalimide decompose above 150° C. to form pores in the thin film. Optical laser microscopy images of the P3HT films with tert-butyl phenyl carbonate and N-(tert-butoxy-carbonyloxy)-phthalimide films baked at 170° C. were taken. Pores in the film with N-(tert-butoxy-carbonyloxy)-phthalimide are clearly visible under the optical laser microscope (FIGS. 3A-3C) compared to plain P3HT, while the pore formation is not as obvious for Tert-butyl phenyl carbonate. P3HT devices with N-(tert-butoxy-carbonyloxy)-phthalimide added as porogen gave a response of 24.9% current decrease on exposure to 25 ppm ethylene for 5 minutes (FIG. 2c). Thus, a 70% increase in response was observed by increasing the interaction area of the sensor layer via introducing higher porosity in the active semiconductor layer.

In order to further enhance the response, a strong receptor additive was chosen to trap the ethylene molecules without compromising the porosity of the thin film. Palladium particles (<1 micron diameter) were added to the semiconductor solution in a glove box. The mixture was then spin coated on the silicon substrates (with gold source and drain electrodes already patterned). By adding 50 wt % of palladium particles to P3HT+N-(tert-butoxy-carbonyloxy)-phthalimide, a response of 30.2% drain current decrease was obtained, equivalent to a 107% increase in the response, was observed (FIG. 2c). On further increasing the wt % of palladium particles to 70%, the semiconductor characteristics were lost completely. Increasing the wt % of palladium particles beyond 50% (equivalent to 100% of the weight of the semiconductor also included) led to a very high density of palladium particles resulting in formation of conductive pathways in the film.

A student t-test was conducted to determine the significance of the increase in sensitivity from the addition of porogen ($p<0.05$) and the further addition of Pd particles ($p<0.005$). This increase was anticipated due to the pores increasing site availability for gas molecules and due to the well-documented binding interactions between Pd and ethylene gas. Thus, a method by which non-specific P3HT can be made to have statistically significant increases in sensitivity of the ethylene analyte was demonstrated.

Figure 4A:
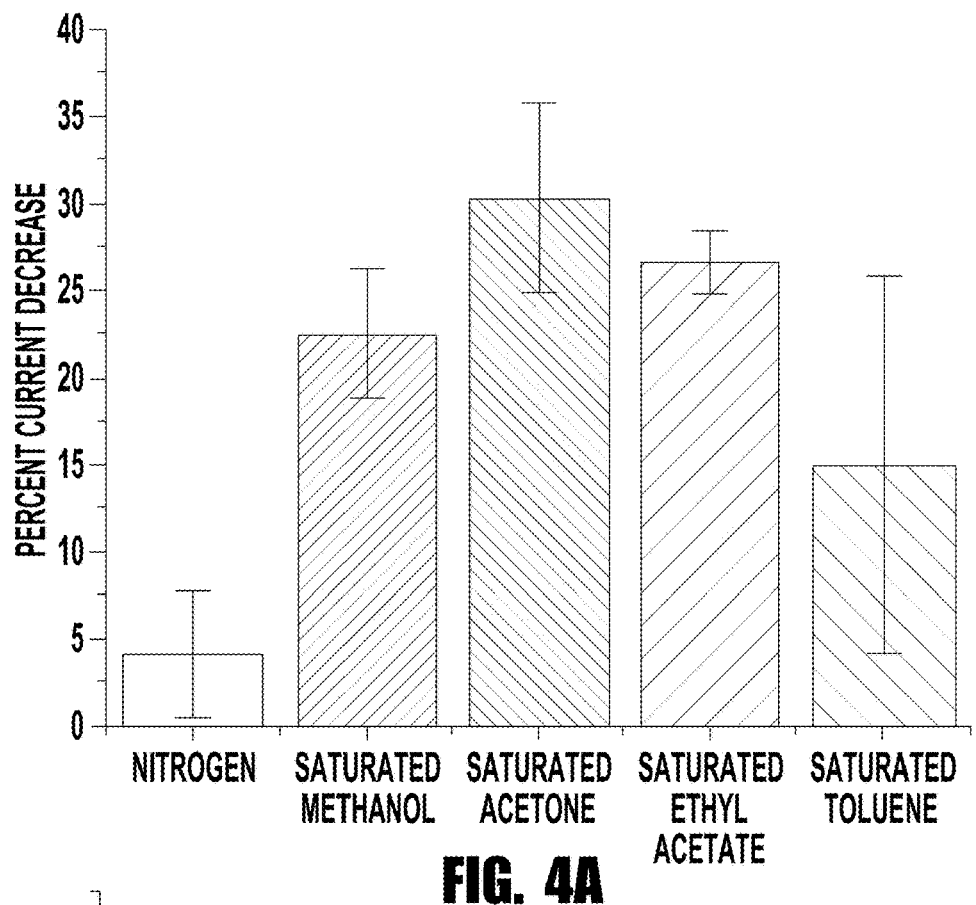
FIGS. 4A and 4B provide (a) selectivity data from saturated solvent conditions and (b) calculated responses per 1000 ppm of solvent in atmosphere.
Figure 4B:
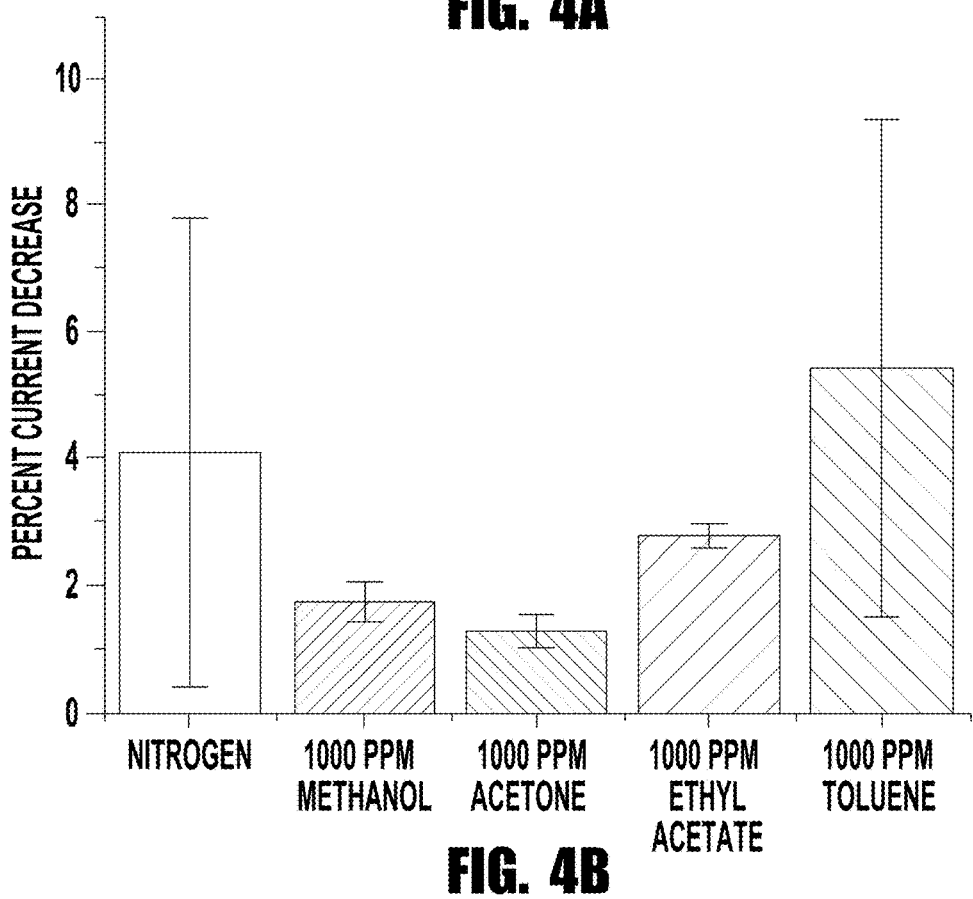

A selectivity study was conducted for this ethylene-sensing platform for common solvents vapors like ethyl acetate, methanol and acetone at saturation concentration. The study was conducted under saturated solvent vapor, with concentrations from one hundred to nearly five hundred times that of ethylene. As the interaction of palladium is expected to be highly specific for ethylene molecules, it is not surprising that this platform is highly selective for ethylene at a much lower concentration than common solvents (FIGS. 4A and 4B). While significant responses were found with all solvents, saturated conditions of any of them would not be expected in an environment where ethylene is being sensed. Additionally, the calculated per-100 ppm response of the solvents is less than 0.5%, well within the simple variance caused by exposure to flowing nitrogen gas, and of course far less than the responses to ethylene.

The inventors have successfully demonstrated a sensitive and selective OFET sensor suitable for effective detection of ethylene at a concentration at or below 25 ppm, far more sensitive than the previously reported OFET ethylene detection. Furthermore, it was shown that the addition of pores to increase overall sensing area of the thin film and palladium nanoparticles to increase ethylene binding are highly constructive for increasing ethylene sensitivity. The numerous possibilities for further tuning this system, such as adjustments in polymer orbital energy levels, pore sizes, and palladium particle diameters, offer promising paths to reaching the sub-ppm sensing level needed for monitoring produce during storage.

Materials and Methods

Highly doped n type silicon used for device fabrication was bought from Si Tech. Palladium particles, Tert-butyl phenyl carbonate ($S_1$) and N-(tert-butoxy-carbonyloxy)-phthalimide ($S_1$) were purchased from Sigma Aldrich. (P3HT) was purchased from Solaris. Ethylene gas with a defined concentration of 25 ppm and 500 ppm in dry nitrogen was purchased from PRAXAIR.

Device Preparation

Highly doped n type silicon wafers with 300 nm silicon dioxide were diced into 1 inch by 1 inch pieces. The wafers were then cleaned using piranha solution (3:1 of sulfuric acid:hydrogen peroxide) followed by sonication in acetone and then in isopropanol for 30 minutes. The wafers were dried using nitrogen gas flow. Gold electrodes (50 nm) were deposited through a shadow mask (channel width/length ratio approximately 308 (77000 µm/250 µm)) at a rate of 0.3 Å/s using physical vapor deposition. The pressure of the deposition chamber was maintained at $<5\times10^{-6}$ torr. P3HT is deposited from a 4 mg/ml solution in chlorobenzene. Palladium particles (50 weight %) were added to a 4 mg/ml solution of $P_3HT$ in chlorobenzene in order to introduce transition metal traps for ethylene in the active semiconductor layer. To further enhance the ethylene sensing performance Tert-butyl phenyl carbonate (25 volume %) and N-(tert-butoxy-carbonyloxy)-phthalimide (25 weight %) were added as porogens to P3HT/Palladium solution. The P3HT/Palladium/porogen mixture is spin coated on silicon/$SiO_2$ substrate (with the predeposited gold electrodes) at 1000 rpm. The devices are baked at 170-degree Celsius under vacuum for 2 hours.

Measurements

Figure 5:
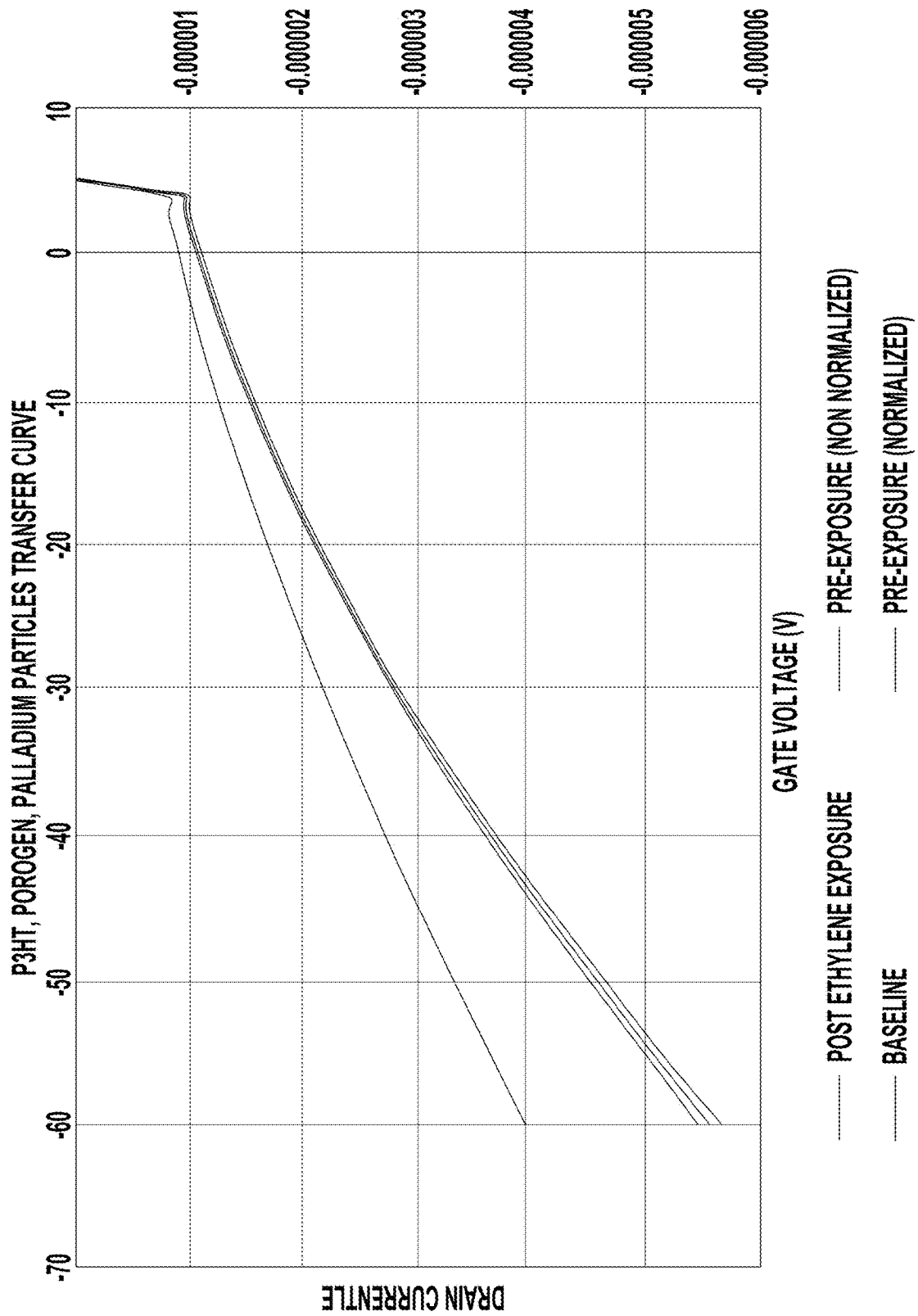
FIG. 5 provides a graph showing P3HT, porogen and palladium particle transfer curves.
Figure 6A:
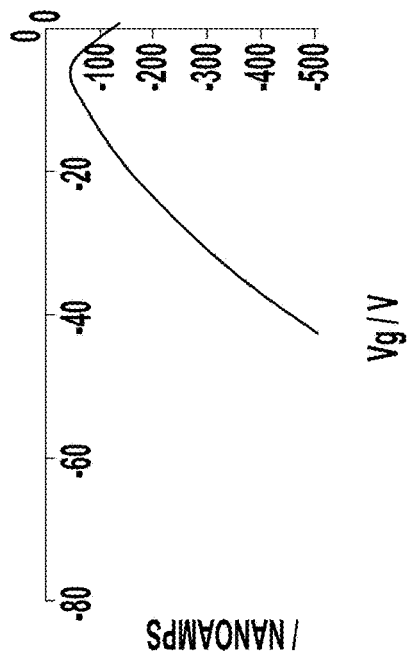
FIGS. 6A-6D provide graphs showing a) Transfer Curve of Proprietary Semiconducting Polymer b) Transfer curve of PQT-12 c) Transfer curve of CoPc d) Transfer curve of CuPc.
Figure 6B:
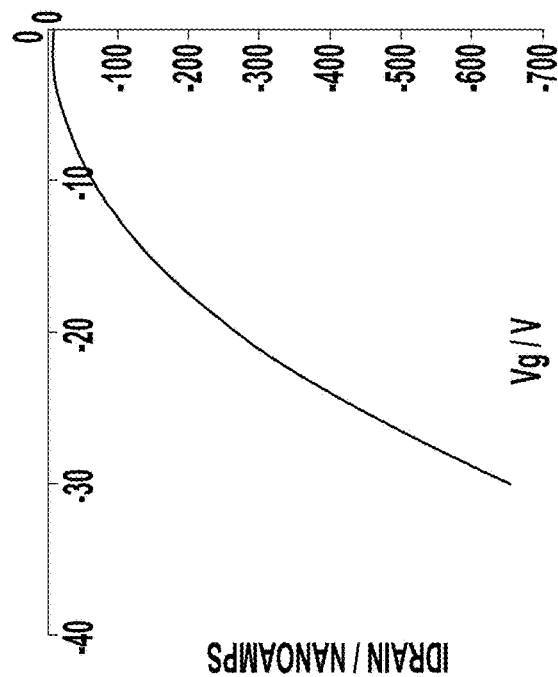
Figure 6C:
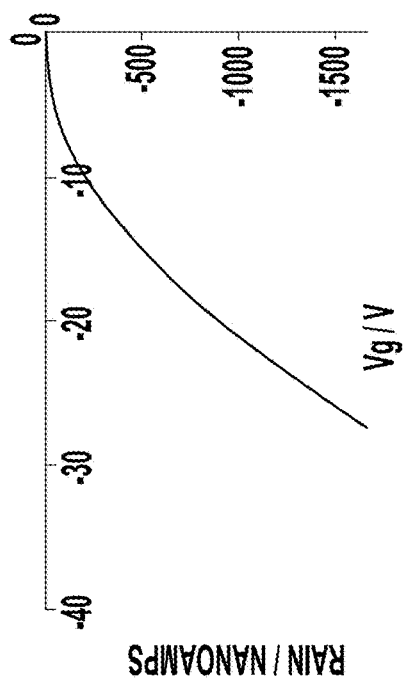
Figure 6D:
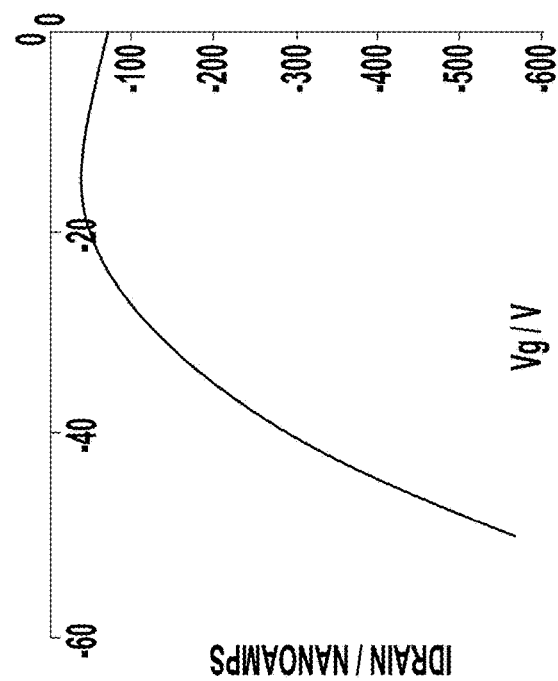

Organic field effect transistor devices with P3HT/Palladium/porogene spincoated film as the active semiconductor films were used as a sensing platform for ethylene sensing. Typical OFET transfer curves are shown in FIG. 5. OFETs were evaluated under Vds=−60V and Vg from 5 to −60 V. All the OFETs were measured using an Agilent 4155C semiconductor analyzer.

Sensing Measurement Description

A home-built, well-sealed chamber with a volume of 1770 ml was used for exposure experiments. Gas for the ethylene experiments was introduced through clean tubing and supplied a steady, known quantity by flowing through the Environics 4040 Series Gas Dilution System for 5 minutes. Devices were quickly transferred back to the sensing platform following exposure to ensure optimum readings. Devices were allowed to come to an equilibrium state before all measurements before gas exposure. This was done by measuring the device response in 5 minute increments and noting drift from starting current response (detailed more below in a discussion of stability). P3HT is not extremely air-stable in this type of device, but after a short amount of time it develops a small (1-4%) and consistent current decrease when measured. This was analyzed and corrected for in data analysis.

For selectivity measurements, a 150 mL flask was corked with a rubber stopper and a device placed inside. Air was removed from the system using a syringe, and replaced with saturated vapor from a sealed bottle of the measured solvent. For 1% saturation measurements, only 1.5 mL of saturated vapor was introduced back into the enclosed environment.

Example 2—Ethylene Detection Based on Organic Field Effect Transistors with Additional Organic Semiconductors Highly doped n type silicon used for device fabrication was bought from Si Tech. Palladium particles, copper phthalocyanine (cupc) and cobalt phthalocyanine (copc), poly(alpha-methylstyrene), tert-Butyl phenyl carbonate and N-(tert-butoxy-carbonyloxy)-phthalimide were purchased from Sigma Aldrich. Proprietary Semiconducting Polymer was generously supplied by Cambridge display technology, XC1360 is a research material donated by Plextronics, and all the other polymers were synthesized in our group using standard methods. Ethylene gas with a defined concentration of 50 ppm and 100 ppm in dry nitrogen was purchased from PRAXAIR.

Highly doped n type silicon wafers with 300 nm silicon dioxide were diced into 1 in. by 1 in. pieces. The wafers were then cleaned using piranha solution (3:1 of sulfuric acid:hydrogen peroxide), followed by sonication in acetone and then in isopropanol for 30 minutes. The wafers were dried using nitrogen gas flow. Gold electrodes (50 nm) were deposited through a shadow mask (channel width/length ratio approximately 308 (77000 µm/250 µm)) at a rate of 0.3 Å/s using physical vapor deposition. The pressure of the deposition chamber was maintained at $<5\times10^{-6}$ torr. Organic semiconductors were either spin coated (from a solution, 4 mg/ml in chorobenzene for poly(3,3'''-didodecylquaterthiophene) (PQT-12) at 60° C. and 9 mg/ml in o-xylene for Proprietary Semiconducting Polymer at 90° C. (heated at least an hour)) or thermally deposited using physical vapor deposition (copper phthalocyanine (cupc) and cobalt phthalocyanine (copc))

Organic field effect geometry was used for sensing. See FIG. 2a. All the OFETs were measured using an Agilent 4155C semiconductor analyzer. A home-built, well-sealed chamber with a volume of 1300 ml was used for exposure experiments.

As ethylene is not a very strongly interacting analyte and can only affect the sensing membrane via delocalized double bond electrons in the structure ($CH_2$=$CH_2$), all the p type organic semiconductors were chosen which would react strongly to an analyte with electron donating tendencies, for preliminary filtering. The list of potential semiconductors includes PQT-12 poly(3,3'''-didodecylquaterthiophene), copper phthalocyanine (cupc) and cobalt phthalocyanine (copc)) and XC1360. PQT-12 was chosen as it has been well established for sensing ammonia, which also has a lone pair of electrons. Besar et al., Org. Electron., 15, 3221-3230 (2014). Copper and cobalt ions are known to form coordination complexes with ligands like ammonia; we wanted to exploit the possibility of ethylene being a potential ligand for these two metals by using copper phthalocyanine and cobalt phthalocyanine. Huang et al., J Am Chem Soc., 134(36), 14650-3 (2012).

The Transfer curves for PQT-12, CuPc, CoPc, and Proprietary Semiconducting Polymer are shown in FIGS. 6A-6D. The ethylene sensitivity was investigated by monitoring the percentage change in the drain current of the OFET device. Table 1 summarizes the exposure experiments for 100 ppm of ethylene for 5 minutes.

TABLE 1

Summary of the exposure experiments, 100 ppm ethylene for 5 minutes

| Active material | % change in current after exposure to 100 ppm ethylene for 5 minutes |
|---|---|
| PQT-12-s | No change |
| PQT-12 | 15.31% decrease |
| PQT-12 + Chloro[1,3-bis(2,6-diisopropylphenyl)imidazol-2-ylidene]copper(I) 10:1 | 19.6% decrease |
| CoPC | 25.26% decrease |
| Proprietary Semiconducting Polymer | 22.46% decrease |
| CuPC | 21.17% decrease |
| XC1360 | 20.8% decrease |
| XC1360 + (1,10-phenantroline)bis(triphenylphosphine)copper(I) nitrate dichloromethane adduct 95% 10:1 | 13.48% decrease |

CoPC gave the highest response of approximately 25.26% to 100 ppm ethylene exposure for 5 min followed by 22.46% for Proprietary Semiconducting Polymer and 21.17% for CoPC. PQT-12 gave a considerably low response of 15.31%. These responses can be attributed to the fact that cobalt and copper both have a tendency to form coordination complexes and so ethylene can interact with these compounds as ligand. Ethylene acts as a trap for the positive charge carriers in the films and hence a decrease in the overall conductivity of the film was observed, and the response was fully reversible. Ethylene is not a very strong ligand, so this interaction should be very temporary in nature leading to a reversible response. For PQT-12, the interaction must be only physical adsorption, which justifies the lower responses.

As ethylene is known to have an affinity to form bond with Copper(1)complexes (Esser et al., Angew. Chemie-Int. Ed. 51, 5752-5756 (2012)), Chloro[1,3-bis(2,6-diisopropylphenyl)imidazol-2-ylidene]copper(I) and Phenanthroline-bis(triphenylphosphine) copper(I) nitrate dichloromethane adduct 95% were added to PQT-12 and XC1360 films in order to introduce some kind of specific interaction between ethylene and the sensing membrane. While chloro[1,3-bis(2,6-diisopropylphenyl)imidazol-2-ylidene]copper(I) increased the response of PQT-12 to 100 ppm Ethylene from 14% to 20%, Phenanthroline-bis(triphenylphosphine)copper(I) nitrate dichloromethane decreased the response to 13% from 20%. In the case of devices with a composite semiconductor film, interaction between the additive and the host film also plays a significant role along with the chemistry between the additive and analyte in determining the effect of additive on the overall sensitivity of the device. For example in case of PQT-12 film the sensitivity of the device is increased due to the affinity of the additive for the analyte while for XC1360 films addition of phenanthroline-bis(triphenylphosphine)copper(I) nitrate dichloromethane actually made the film more dense and as a result there was a decrease in the response.

Figure 7B:
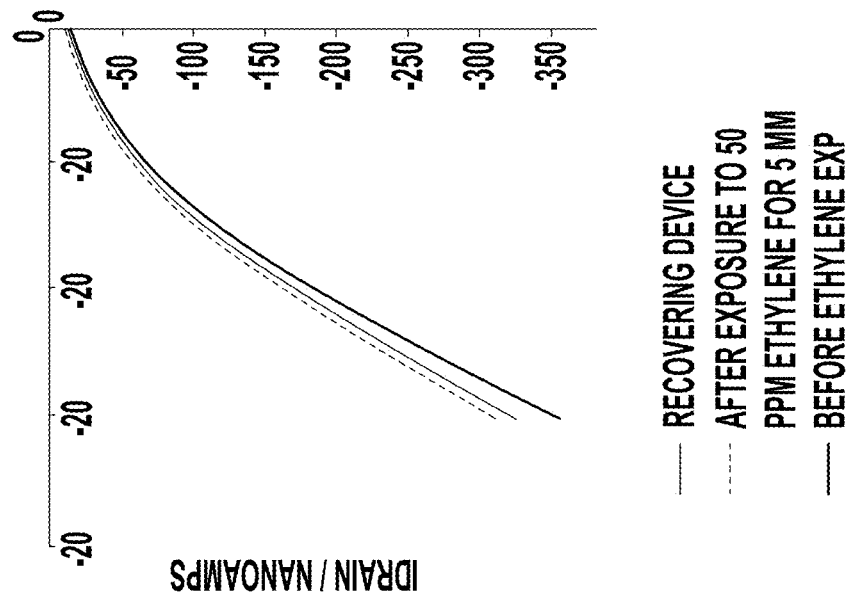
FIGS. 7A and 7B provide graphs showing a) Proprietary Semiconducting Polymer, 100 ppm exposure, 22% decrease in current b) Proprietary Semiconducting Polymer, 50 ppm exposure, 10% decrease in current.
Figure 7A:
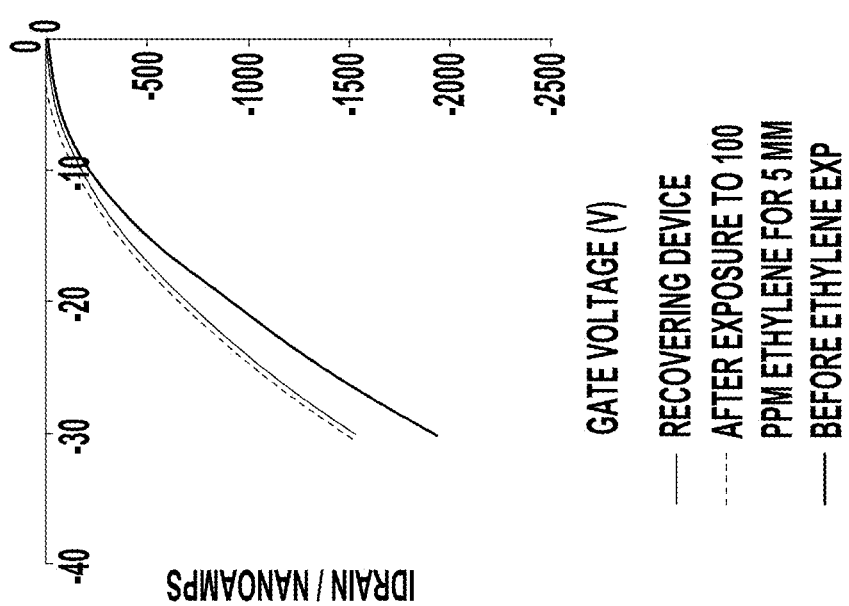

Reducing the number of physical vapor deposited steps is important when making a low-cost ethylene sensor. Among the three highly sensitive organic semiconductor layers (Copc, CuPC and Proprietary Semiconducting Polymer), Proprietary Semiconducting Polymer was the only solution processible choice and hence it was selected for further development. Proprietary Semiconducting Polymer gave a 22% decrease in drain current upon exposure to 100-ppm ethylene for 5 minutes and 10% decrease in drain current on exposure to 50-ppm ethylene for 5 minutes (FIGS. 7A and 7B). Thus decreasing the ethylene concentration directly affects the % decrease in the response.

In some embodiments, palladium particles were mixed into the polymer spincoating solution to produced films with Pd weight % given below. Gold stripes 200 microns apart were vapor-deposited to serve as source and drain contacts of a field-effect transistor. Polymer and oxide were scratched away from a corner of the substrate so that the silicon wafer could be contacted with a gate electrode for operation of the transistor. Samples were stored from 1-3 days in air before testing. The transfer curves (sweeps of gate voltage from zero at constant drain voltage) of transistors were recorded before, immediately (about one minute) after, and longer times after 5 minutes' exposure to ethylene gas at concentrations given below. Table 2 below gives maximum currents recorded on transfer curves under the given conditions.

Figure 8B:
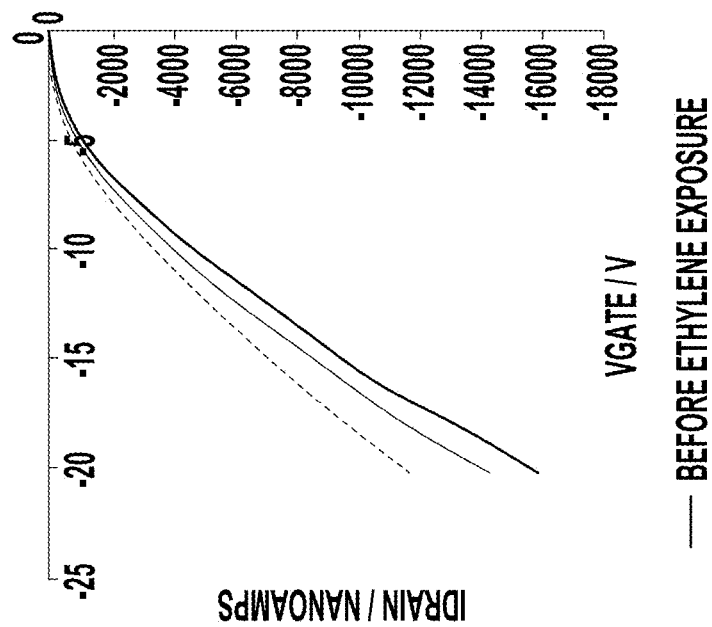
FIGS. 8A and 8B provides graphs showing a) Proprietary Semiconducting Polymer with 40% palladium particles, 18% decrease in drain current, 50 ppm Ethylene b) Proprietary Semiconducting Polymer with 50% palladium particles, 27% decrease in drain current, 50 ppm Ethylene.
Figure 8A:
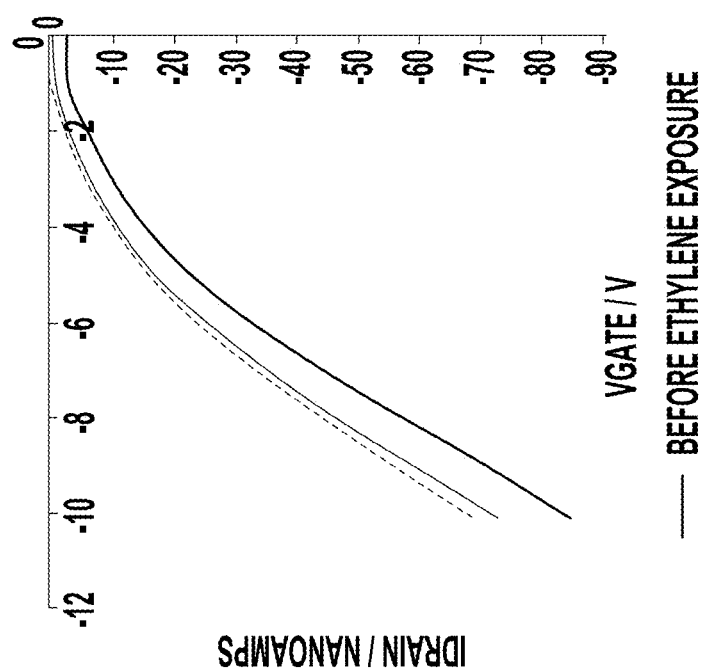

Palladium particles (<1 micron diameter) were added to the semiconductor solution in the glove box. The mixture was then spin coated on the silicon substrate. Semiconductor films with 40 wt % gave 18% decrease in drain current on exposure to 50 ppm ethylene for 5 minutes. Increasing the wt % of palladium to 50% increased the response to 27%, FIGS. 8A and 8B. On further increasing the wt % of palladium particles to 70% the semiconductor characteristic was lost completely. Increasing the wt % of palladium particles beyond 50% led to a very high density of palladium particles resulting in formation of a conductive pathway. Thus palladium can be successful incorporated as a receptor for ethylene and 50 wt % of palladium in a Proprietary Semiconducting Polymer film can increase the sensitivity of the film by 100%.

TABLE 2

Maximum Currents Recorded on Transfer Curves

| Sample # | Pd wt % | ppm ethylene | Drain and gate voltage (V) | Current before exposure, microamps | Current 1 min after exposure | Longer time after exposure (min.) | Current after longer time |
|---|---|---|---|---|---|---|---|
| 1 | 0 | 100 | 30 | 2.0 | 1.5 | — | 1.5 |
| 2 | 0 | 50 | 16 | 0.34 | 0.30 | 7 | 0.32 |
| 3 | 0 | 50 | 50 | 0.51 | 0.45 | — | — |
| 4 | 0 | 50 | 50 | 0.90 | 0.83 | — | 0.87 |
| 5 | 40 | 50 | 10 | 0.085 | 0.070 | — | 0.073 |
| 6 | 50 | 50 | 20 | 16 | 11 | — | 14 |

To test the reproducibility of set of nominally similar devices, three transistors were made with 50 wt % Pd particles in Proprietary Semiconducting polymer. Each transistor was tested for response to 50 ppm ethylene exposure for five minutes. The resulting current decreases were 24.7% with a standard deviation of 1.5 percentage units. Furthermore, each device showed recovery of about 75% of the current decrease five minutes after the exposure.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An ethylene-sensitive sensor, comprising:
    a power source;
    an ethylene-sensitive semiconductor component electrically connected to the power source, the semiconducting component comprising a semiconducting organic compound combined with palladium particles and a porogen to introduce pores into the semiconducting organic compound, increasing surface area of the semiconducting organic compound;
    an input electrode electrically connected to the semiconductor component; and
    an output electrode electrically connected to the semiconductor component;
    wherein the semiconductor component is at least partially exposed such that it can be contacted by a vapor.

2. The ethylene-sensitive sensor of claim 1, wherein the ethylene-sensitive sensor further comprises a gate electrode and the ethylene-sensitive semiconductor component is part of a field effect transistor.

3. The ethylene-sensitive sensor of claim 1, wherein the semiconducting organic compound, the input electrode, and the output electrode, are in contact with a silicon dioxide layer positioned over a silicon layer.

4. The ethylene-sensitive sensor of claim 1, wherein the semiconducting organic compound is a p-type organic semiconductor.

5. The ethylene-sensitive sensor of claim 1, wherein the semiconducting organic compound includes an organic group selected from the group consisting of thiophene, phenylene, selenophene, fluorene, naphthalene, ethylene, ethynylene, cyclopentadiene, silacyclopentadiene, benzothiadiazole, benzoxadiazole, diketopyrroleopyrrole, and isoindigo.

6. The ethylene-sensitive sensor of claim 1, wherein the semiconducting organic compound is a semiconducting polymer.

7. The ethylene-sensitive sensor of claim 6, wherein the semiconducting polymer is a thiophene polymer.

8. The ethylene-sensitive sensor of claim 7, wherein the thiophene polymer is poly(3-hexylthiophene-2,5-diyl) (P3HT) or poly(3,3'''-didodecylquarterthiophene) (PQT12).

9. The ethylene-sensitive sensor of claim 1, wherein the porogen is N-(tert-butoxy-carbonyloxy)-phthalimide.

10. The ethylene-sensitive sensor of claim 1, wherein the ethylene-sensitive sensor is flexible.

11. A method of detecting an ethylenic compound using the ethylene-sensitive sensor of claim 1, comprising contacting a vapor of interest with the ethylene-sensitive sensor having an output voltage or current, and determining that an ethylenic compound is present in the vapor of interest if this contact causes a change in the output voltage or current of the ethylene-sensitive sensor.

12. The method of claim 11, wherein the ethylene-sensitive sensor further comprises a gate electrode and the semiconductor component of the ethylene-sensitive sensor is part of a field effect transistor.

13. The method of claim 11, wherein the ethylenic compound is ethylene.

14. The method of claim 13, wherein the vapor of interest is produced by fruit.

15. The method of claim 11, wherein the method of detecting the ethylenic compound includes the step of determining the amount of ethylenic compound present in the vapor.

16. The method of claim 11, wherein a concentration of 50 ppm or more of the ethylenic compound is sufficient to cause a detectable change in the output voltage or current of the ethylene-sensitive sensor.

* * * * *